United States Patent [19]

Bedard et al.

[11] Patent Number: 5,384,144
[45] Date of Patent: Jan. 24, 1995

[54] PSYLLIUM ENRICHED PASTA PRODUCTS AND METHOD FOR MAKING SAME

[75] Inventors: Aimee M. Bedard, Kalamazoo; Grace H. Lai, Portage, both of Mich.; Richard D. Wullschleger, Blandon, Pa.; James G. Kincaid, Battle Creek, Mich.

[73] Assignee: Kellogg Company, Battle Creek, Mich.

[21] Appl. No.: 123,342

[22] Filed: Sep. 17, 1993

[51] Int. Cl.$^6$ .................................. A23L 1/0526
[52] U.S. Cl. .................. 426/557; 426/451; 426/573
[58] Field of Search ............ 426/557, 451, 573

[56] References Cited

U.S. PATENT DOCUMENTS

| | | | |
|---|---|---|---|
| 3,148,114 | 9/1964 | Fahrenback et al. | 167/55 |
| 3,574,634 | 3/1971 | Singer | 99/83 |
| 4,348,379 | 9/1982 | Kowalsky et al. | 424/34 |
| 4,766,004 | 8/1988 | Moskowitz | 426/658 |
| 4,849,222 | 7/1989 | Broaddus | 424/195 |
| 4,950,140 | 8/1990 | Pflaumer et al. | 424/439 |
| 5,015,486 | 5/1991 | Franssell et al. | 426/243 |
| 5,024,996 | 6/1991 | Ringe | 514/54 |
| 5,026,689 | 6/1991 | Ringe et al. | 514/57 |
| 5,035,903 | 7/1991 | Silva | 426/19 |
| 5,095,008 | 3/1992 | Pflaumer et al. | 514/23 |
| 5,122,378 | 6/1992 | Hauser et al. | 426/242 |
| 5,133,984 | 7/1992 | Murphy et al. | 426/496 |
| 5,192,564 | 3/1993 | Abdelrahman | 426/19 |
| 5,223,298 | 6/1993 | Wullschleger et al. | 426/549 |
| 5,227,248 | 7/1993 | Wullschleger et al. | 428/549 |

*Primary Examiner*—Donald E. Czaja
*Assistant Examiner*—Mary S. Mims
*Attorney, Agent, or Firm*—Felfe & Lynch

[57] ABSTRACT

The invention provides for a pasta product, that is enriched with a psyllium composition, wherein the psyllium is present in an amount from about 1.0 g to about 5.0 g per two ounces of pasta product. Also provided is a method to incorporate a psyllium product which comprises pretreating the psyllium so as to prepare it for combination with a pasta flour, such as semolina flour. The resulting pasta product has a sufficient amount of psyllium to alter the level of serum cholesterol in the consumer.

22 Claims, No Drawings

PSYLLIUM ENRICHED PASTA PRODUCTS AND METHOD FOR MAKING SAME

FIELD OF THE INVENTION

This invention relates to psyllium-enriched pasta products. The pasta products may be administered to humans and animals susceptible to or afflicted with hypercholesterolemia to lower serum cholesterol or to individuals in need of dietary regulation. The invention also relates to the production of the pasta products, in which psyllium is prewetted prior to incorporation into the pasta product.

BACKGROUND OF THE INVENTION

Psyllium is a known mucilaginous material which has found extensive use in bulk laxatives. The source of psyllium is the seeds of plants of the Plantago genus, which grow in certain sub-tropical regions. Since it is believed by those skilled in the art that the active ingredient of psyllium is the psyllium seed gum, which is located primarily in the seed husk, present technology uses the ground seed husk as the source of psyllium. However the whole seed is also known as a psyllium source, as well as the dehusked psyllium seed.

It is well known that psyllium decreases plasma triglycerides and LDL cholesterol, particularly in humans. The specific use of a psyllium hydrophilic muciloid to lower cholesterol in serum was documented by Anderson et al., Arch. Intern. Med. Vol. 148, Feb 1988, 292–296 (1988), Anderson et al., Am J. Clin Nutr. Vol.56, p. 93–98, (July 1992). It has been theorized that psyllium, which belongs to a class of gel forming soluble fibers, disrupts the absorption or metabolism of cholesterol by binding, entrapping, absorbing, or otherwise interfering with the reabsorption of bile acids across the intestinal lumen. It is also theorized that the soluble fiber interferes with the intraluminal formation of micelies, resulting in decreased cholesterol and bile acid reabsorption. The end result is that more bile acids and dietary cholesterol are ultimately excreted in the feces, resulting in a decreased level of serum cholesterol.

However, due to its mucilaginous nature, psyllium acquires a slimy or adhesive texture and mouthfeel upon hydration. Psyllium normally forms a gelatinous mass when contacted with water and exhibits poor dispersibility and mixability in water. Psyllium also develops a distinctive, undesirable flavor in the presence of heat and moisture which further limits its use in food products. This slimy mouthfeel is unpalatable and, accordingly, various additives have been incorporated in psyllium-containing ingestible compositions in order to mask the undesirable texture and mouthfeel of the psyllium.

Notwithstanding the undesirable flavor and texture imparted to an ingestible composition by psyllium or psyllium husks, various psyllium-containing foodstuffs have been proposed which purport to take advantage of the natural digestion regulation properties of psyllium, or the satiating or "fullness-feeling" effect of psyllium. See, for example, U.S. Pat. Nos. 3,574,634 and 4,348,379.

In addition, it has been suggested, for example, in U.S. Pat. No. 3,148,114, that whole psyllium husks, such as the ground husks of the seed of Plantago psyllium, lower blood cholesterol upon oral administration thereof. Further, it has also long been known to use small quantities of psyllium, such as less than 1%, as a thickener in foodstuffs, such as in ice cream, puddings and the like.

Finally, U.S. Pat. No. 4,849,222 discloses a medicament composition for reducing blood cholesterol levels in humans and lower animals which comprises a mixture of psyllium seed gum, or source of psyllium seed gum, and a nonabsorbable, nondigestible polyol polyester.

Attempts have been made to incorporate psyllium into foodstuffs, so that the fiber can be consumed as part of a regular meal or other aspect of a normal diet, without any connotation or association with medicines, as well as with acceptable organoleptic properties. Examples of the patent literature involving psyllium incorporated into foodstuffs are U.S. Ser. Nos. 817,244 and 819,569 both filed Jan. 6, 1992, now U.S. Pat. Nos. 5,223,298 and 5,227,248, both of which are incorporated by reference. These patents teach psyllium containing ready to eat cereals. Additional examples of cereals containing psyllium are set forth by Moskowitz, U.S. Pat. No. 4,766,004; Ringe U.S. Pat. No. 5,024,996; and Ringe et al., U.S. Pat. No. 5,026,689. Other foodstuffs which include psyllium are taught in U.S. Pat. Nos. 5,095,008 and 5,950,140 both of which teach cookies with incorporated psyllium, U.S. Pat. No. 5,015,486, which teaches microwaveable muffins, and U.S. Pat. No. 5,024,996 which teaches almond paste containing compositions, such as marzipan. U.S. Pat. No. 5,164,216 describes bread suitable for microwaving which contain required levels of shortening and fiber. Psyllium muciloid is mentioned as a potentially useful fiber source; however, no examples of its use are given, nor is there any discussion of problems associated therewith.

While it is clearly desirable to incorporate psyllium into food products, the mucilaginous nature of the material render normal preparation processes unsuitable for use. Indeed, as the following examples will show, successful incorporation of psyllium into a pasta product requires that the psyllium be prewet prior to combination with other ingredients.

The psyllium-enriched pasta, manufactured according to this invention, results in an improved pasta product as a result of a psyllium prewetting process. The pasta product is manufactured from a dough which includes a prewetted psyllium which attracts more moisture and thus has a higher moisture content than conventional doughs.

It is therefore a principal object of this invention to provide for an effective and economically produced food composition comprising psyllium in a pasta product.

It is a further object of this invention to provide for a pasta composition containing psyllium which is palatable and suitable for human consumption in a food product while providing the benefits of lowered serum cholesterol levels.

SUMMARY OF THE INVENTION

This invention provides for a pasta food product enriched with psyllium, where the psyllium is pretreated which renders it soluble and dispersible in a pasta product. Alternate methods for making the pasta product are also disclosed herein.

DETAILED DESCRIPTION OF THE INVENTION

The following controls and examples set forth a series of experiments to show the efficacy of pretreating the psyllium prior to incorporation with other pasta ingredients. Generally the pasta product containing prewetted psyllium produce an organoleptically acceptable product. The experiments set forth a number of attempts to produce a psyllium incorporated pasta product which has satisfactory product characteristics (e.g., firm enough), and which is organoleptically acceptable.

A 98% purity extruded psyllium product can be used as the starting material. The 98% purity extruded psyllium can be prepared utilizing the following parameters. The psyllium is extruded through a WP/twin screw extruder at a minimum temperature of 240° F. The moisture of the material in the extruder is maintained at approximately 15.5% to about 17.5% water during the extrusion process. The approximate feed rate for the psyllium product is about 15 to 17 kg per minute, preferably at about 16 kg per minute. The finished 98% purity extruded psyllium product has a moisture content of about 6-10%.

Psyllium which has been cold extruded can also be used. The psyllium is first treated with flour, sugar and Myvaplex TM KODAK (mono and diglycerides) and extruded to form a pellet by the "cold" process. The pellets are dried and ground for use as raw material. The psyllium ground from the cold formed pellets is then subjected to the prewetting process as described previously. This is further described in example 4.

The pasta product may also be manufactured using a "hot" extruded psyllium pellet. The hot extruded pellets are manufactured in a process similar to the cold form pellets with the exception of the absence of Myvaplex TM, and the temperatures at which the extrusion takes place. This is further described in example 6.

Often with conventional pasta processing, the dry ingredients are mixed with water and then extruded. The conventional doughs have a moisture content of approximately 30%, whereas the psyllium-enriched pasta is hydrated to a moisture content of approximately 35% to 45% moisture prior to dehydration. In addition, prewetting the psyllium also improves processing and removes some of the characteristic psyllium odors and flavors.

The process of pasta drying is also critical in the manufacture of pasta. The appropriate rate of drying must be determined. Often if the pasta product is dried too quickly, the outer layer will shrink much faster than the inner and the differential drying process will result in cracking the pasta. On the other hand, if the pasta is dried too slowly, problems arise with the growth of airborne bacteria and molds which may spoil the dough. The product according to the present invention is allowed to dry in a dehydrator for approximately 10 to about 14 hours.

The examples which follow show that the type of psyllium used can vary. One may use extruded psyllium, whether extruded via hot or cold processes, or "neat" psyllium, as long as the material is prewetted before incorporation into the pasta flour. This invention will be better understood by reference to the following controls and examples, which are included here for purposes of exemplification and are not to be construed as limitations.

Control 1

A pasta product was prepared by combining 399.5 g of semolina flour, and 54.5 g of 98% purity extruded psyllium treated with citric acid. Following the premixing of these two ingredients, five whole eggs (248 g), and water (31.6 g) were added. The resulting dough was mixed by hand for three minutes, and then passed through a home pasta cutting machine. The pasta was dried for five minutes, and then cooked in boiling water for 10 minutes.

The dough was difficult to knead through the machine, and tore. Further, the dough was "short", and gritty. The longer the dough sat, the more difficult it was to process.

Control 2

Semolina flour (453.59 g) was first blended with psyllium (60.14 g). Water (312 g) was added to the semolina flour/psyllium blend. The dough was first kneaded by hand and then kneaded through a hand-cranked pasta machine. The dough was reduced in thickness by passing it through the machine and changing the gap settings.

However the dough was tough and difficult to knead by hand. The dough also did not knead or process well as it passed through the pasta machine. The texture of the end product was mushy after cooking without a strong psyllium taste. The pasta product had a palatable flavor. The product was speckled and grayish brown in color.

Control 3

Semolina flour (399.5 g) and psyllium (54.5 g) were preblended. Five egg whites (141 g) were added to the semolina flour/psyllium blend to form the pasta dough. The pasta dough was processed according to control 2. The noodles were allowed to air dry for 20 minutes in order to prepare the outer surface for cooking. After cooking for 7 minutes in boiling water, the end product tasted like rubber. The pasta had an unpleasant psyllium odor and had a slimy, mushy texture after cooking. The appearance was slimy after cooking, as was the water in which the pasta was cooked.

Control 4

Semolina flour (452.36 g) was premixed with psyllium (61.35 g) premixed with 2% modified corn starch. The corn starch was added to reduce the rate at which psyllium absorbs water. Water (317.8 g) was then added to the semolina flour/psyllium/corn starch mixture. The longer the dough was processed, the poorer the resulting pasta product. After cooking, the noodles were weak and broke apart easily. The product had no off odor, but the flavor was not optimal.

Control 5

A 75% psyllium pellet was produced by mixing the psyllium with rice flour, sucrose, and annatto color. The pellets were dried and then ground through a Wiley Mill into a powder and used as raw material. This ground psyllium (62.33 g) was then blended with semolina flour (446.74 g). The semolina flour/psyllium blend was then mixed with water (317.8 g) and the dough processed as usual. The noodles were cooked for 7 minutes. The pasta had an off-flavor and odor but was still palatable. The texture was firm and appearance was speckled. The cooking water was a bit slimy.

Example 1

The foregoing controls demonstrate experiments to develop an organoleptically acceptable pasta product using non-prewetted psyllium. The following examples demonstrate experiments to develop a pasta product using prewetted psyllium.

A pasta dough which contained the following ingredients: annatto color, semolina flour and psyllium, at 0.01% 87.99% and 12%, respectively, (all ingredients presented as weight percent, on a dry basis) was prepared in the following manner:

The annatto was combined with 0.6 lb of water. The psyllium and semolina flour were combined, dry, and then the annatto solution was added. The resulting mixture was too dry to knead, so an additional 100 g of water were added. Extrusion was still not as successful as example 2, although the flavor was similar to the flavor of the product of example 2 described infra. The moisture of the total system was 35.2%. Extrusion was much easier using the processes of example 2.

Example 2

A coloring solution was prepared by mixing 0.6 lb of water with 0.09 g (0.01% on a dry weight basis) of annatto. This was then combined with 2 lbs. of semolina flour in a Hobart Mixer. The moisture content of this ingredient is about 32.3%.

Separately, 120.29 grams of psyllium was prewetted with an additional 0.6 lb of water. (The total moisture content was 72.2%). The prewetted psyllium was then combined with the moistened semolina flour, and mixed to form a dough. (Total moisture content of the dough, following this process step, is 42.2%) The resulting dough was marbled in appearance and had a nice consistency. The dough color achieved was more uniform when the annatto was added to the semolina flour than when it was added to psyllium.

The dough, when extruded using a standard pasta mill, extruded well through the pasta die. As it dried, the color of the pasta darkened. The end product had a good color and good, bland pasta flavor.

Example 3

The following ingredients were combined in a pasta dough: (all ingredients presented as weight percent, on a dry basis):

| Annatto color: | 0.01% |
|---|---|
| psyllium: | 6.00% |
| semolina flour: | 93.97% |

Specifically, the annatto color was mixed with 0.6 lb of water. This liquid was then used to prewet the psyllium. In a separate step, the semolina flour was mixed with 0.6 lb of water, and this was then combined with the prewetted psyllium.

The dough extruded well and the color was uniform after extrusion. The pasta was cooked for 10 minutes. The end product had good flavor and texture.

The moisture content of the semolina flour/water mixture was 31.5%. The moisture content of the prewetted psyllium was 84%. The moisture content of the total dough was 42.6%.

Example 4

The following example demonstrates the efficacy of the use of psyllium products obtained using cold extrusion and prewetting. Psyllium pellets (50%) were prepared using a cold extrusion process. They were then ground in a Wiley Mill at #1 setting, to obtain a ground pellet product.

The following ingredients were combined to form the 50% cold extrusion pellets:

| 55.6 lbs | rice flour |
|---|---|
| 48.0 lbs | sucrose |
| 109.9 lbs | psyllium 98% purity |
| 2.0 lbs | Myvaplex TM |

The cold extrusion process proceeds by extruding the above ingredients through a WP twin screw extruder to form psyllium pellets. A cool water bath or jacket can be applied to the extruder so as to maintain the temperature during the extrusion process. The extruder, preferably, incorporates a means to measure the temperature during the extrusion at two zones. Zone 1 is the point at which the mixture is fed through the extruder. Zone 2 is where the mixture is substantially mixed and extruded. During cold extrusion, the temperature maintained in zone 1 is about 60° to about 80° F., preferably the temperature is about 73° F. The temperature in zone 2 is kept at about 160° to about 180° F., preferably the temperature in zone 2 is about 169° F. The pellets are then extruded through a die and dried for about 50 to 90 minutes, preferably 70 minutes, at about 150° F. to a maximum of 200° F., to a moisture content of approximately 6-10%, preferably about 8%.

After the pellets were formed, they were ground to prepare the psyllium powder.

The ground psyllium, semolina flour, and annatto were used to prepare a pasta dough. The amount of the ingredients used were: 23.5%, 76.47%, and 0.01%, respectively (ingredients measured on a dry weight basis). The annatto color was mixed with 0.66 lb of water and the psyllium was prewet with another 0.6 lb of water. The dough was extruded into noodles, which were dried. Specks of psyllium were visible and the dried product cooked faster than a product made with standard psyllium.

Example 5

The following example demonstrates the efficacy of using 90% cold extruded pellets which were formed and ground similar to example 4. A pasta dough containing 13.07% ground psyllium pellets (dry weight basis), prewetted with 0.6 lb water was produced. Annatto color was mixed with 0.6 lbs of water and 86.92% semolina flour. The proportions of prewetted psyllium, semolina, and annatto color, were 13.07%, 86.92% and 0.01%, respectively, by dry weight of the pasta dough. The dough was mixed, extruded and the noodles were dried. The pellet specs were visible in the extruded noodle. The cooked noodles were more rubbery and less fragile than those of example 4.

Example 6

The following example demonstrates the efficacy of using psyllium products obtained via hot extrusion. Psyllium nuggets (50%) were prepared using a hot extrusion process. The 50% hot extruded psyllium pellets were prepared in the same manner as the 50% cold extrusion pellets with the exception of the temperature at which the extrusion took place.

During hot extrusion, the temperature maintained in zone 1 is approximately 140° to 160° F., preferably the temperature is about 150° F. The temperature in zone 2 is kept at approximately 280° to 300° F., preferably the temperature in zone 2 is about 290° F. The pellets are then extruded through a die and dried for about 50 to 90 minutes, preferably 70 minutes, at about 150° F. to a maximum of 200° F., to a moisture content of approximately 6–10%, preferably about 8%. The hot extruded pellets were then ground in a manner similar to those in the example 4.

A pasta dough consisting of 23.52% (dry weight basis) ground extruded psyllium pellets was prewetted with 0.6 lb. water. The pasta dough also contained 76.47% (dry weight basis) semolina flour mixed with 0.6 lbs of water and 0.01% annatto color, as measured by dry weight basis of the pasta dough. The ground hot extruded pellets absorbed water better than cold extruded pellets. The noodles extruded well. The noodles were dried for 10 hours. After drying, the noodles were cooked. These noodles cooked faster than products using pure psyllium. The texture and appearance of cooked noodles was good. The end product was preferred over examples 4 and 5.

Example 7

The cholesterol lowering effect of the psyllium enriched dough of this invention on certain individuals is confirmed by the following study.

Over the course of six months, a long term intervention study is conducted to test the effect of psyllium enriched products on the level of serum cholesterol on sample size of 250 hypercholesterolemic individuals. Individuals chosen for this study are at risk for mild abnormalities in their cholesterol levels. Generally, the study targets individuals with plasma LDL-cholesterol levels at 130 to 220 mg/dl, with the proviso that their triglycerides levels are less than 300 mg/dl. There is an initial eight week dietary instruction and stabilization period where lipid criteria is ascertained.

According to the protocol of the intervention study, the individuals participating in the study are divided into four groups. The groups are administered varying number of servings of psyllium enriched food products to determine whether there is a dose dependent hypocholesterolemic effect. The participants are given a choice of the following psyllium enriched food products: R-T-E- cereal, bread, snack bars, and pasta, which are packaged in zero and 3 mg psyllium servings.

Group A is given three servings of the placebo product per day and is not administered a psyllium food product at all.

Group B is given two servings of the test product and one serving of the placebo product per day.

Group C is given one serving of the test product and two servings of the placebo product per day.

Group D is given three servings of the test product per day.

The serum cholesterol levels are tested periodically during the study by taking blood samples and determining serum cholesterol levels.

The cholesterol levels decrease from baseline over the course of the study indicating the hypocholesterolemic effect of psyllium enriched products. The study further shows that the decrease in serum cholesterol is in proportion to the dosage units of psyllium product ingested.

Example 8

A study was also conducted to test the efficacy of psyllium enriched products in reversing the rise in plasma total cholesterol in hamsters fed a diet with added cholesterol.

The hamsters were administered a diet consisting of approximately, 20% protein, 14% fat, 15% sugar, 1% NaCl. The amount of total dietary fiber was targeted at between 5–10%, which includes non-soluble and soluble fiber.

The control group was given a food product without added cholesterol (Product A) and with added cholesterol (Product B). The control product with added cholesterol (Product B) and the pasta test product (Product C) contained about 0.125% cholesterol.

The control products without and with added cholesterol (products A and B) and the psyllium enriched pasta product (Product C) contained the following ingredients as a percentage of the entire composition:

| | A | B | C |
|---|---|---|---|
| 1. vitamin/mineral amino acid mixture | 7.95% | 7.95% | 7.95% |
| 2. Test Material | — | — | 39.7 |
| 3. wheat bran | 24.0 | 24.0 | 9.3 |
| 4. Casein | 18.0 | 18.0 | 16.6 |
| 5. Safflower Oil | 4.0 | 4.0 | 4.5 |
| 6. Sucrose | 14.3 | 14.3 | 12.9 |
| 7. NaCl | 0.99 | 0.99 | 0.97 |
| 8. Starch | 23.8 | 23.6 | 1.0 |
| 9. Cholesterol | — | 0.125 | 0.125 |
| 10. Beef Tallow | 7.0 | 7.0 | 7.0 |

The level of total cholesterol in hamsters fed with the control product with added cholesterol and the psyllium pasta product were compared. It was found that the serum cholesterol levels for hamsters fed with Product A without added cholesterol, measured in mg/dl was 157.0±31.0. The total cholesterol level of hamsters fed with Product B and of hamsters fed with psyllium enriched Product C, decreased from 221.7±27.7 to 165.8±17.6. This study shows that a psyllium enriched pasta product fed to hamsters on an elevated cholesterol diet reduces the level of total cholesterol.

The psyllium pasta product now having an established hypocholesterolemic effect on an elevated cholesterol diet was then administered to individuals for a taste preference test comparing conventional and psyllium enriched pasta.

Example 9

The following test was carried out to determine the overall preference for standard pasta and pasta with psyllium.

The control low fiber pasta and psyllium enriched pasta was produced according to Applicants' specifications.

Fifty-six panelists were given a one-third cup of pasta with two tablespoons of tomato sauce. The panelists were asked to determine which pasta they preferred. Thirty-three of the fifty-six panelists preferred the control low fiber pasta, p-value=0.0230. A significance criteria of p=0.05 was set prior to this test. Based on this test, no preference was found between the standard low fiber pasta and the pasta made with psyllium when served with tomato sauce.

The foregoing controls and examples show that where psyllium is pretreated according to the processes delineated, it can be successfully incorporated into a food product, i.e., pasta. The pretreatment of psyllium is accomplished by combining the psyllium with water prior to mixing into a dough.

The key ingredient of this invention is the prewetted psyllium. Prewetted psyllium is prepared by adding water to the psyllium and allowing the mixture to temper before combining with other ingredients. It is also possible to combine the prewetted psyllium with the pasta ingredient, e.g., semolina flour, and then allow the dough to temper, as described below. It is preferred to combine the water and psyllium in a ratio of from about 0.75:1 to 1.25:1 (by weight). A ratio of 1:1 is particularly preferred.

The tempering period for the prewetted psyllium may vary. The key aspect is that the prewetted psyllium possesses a free flowing nature as compared to the non-prewetted material. If the prewetted material is allowed to temper for more than about 24 hours, this property is lost. Moreover, an extensive time period may encourage the growth of microorganisms. Therefore, the prewetted psyllium should not be permitted to temper for more than about 24 hours. It is preferred to allow it to temper overnight (10-12 hours) or even less. It is especially preferred to temper the psyllium no more than about two to five hours, and most preferably 30 minutes after prewetting treatment.

The pasta product is preferably extruded soon after the pasta dough is combined with the prewetted psyllium. However, the psyllium can also be allowed to temper after the prewetted psyllium is combined with the pasta ingredients, e.g. semolina flour. The pasta dough containing prewetted psyllium must not be allowed to temper more than one to two hours. Psyllium can be successfully incorporated whether the psyllium is allowed to temper after it is prewet, before the addition of a pasta ingredient or after the prewetted psyllium is combined with the pasta ingredients.

The amount of psyllium incorporated into a pasta product may vary from about 1.0 gm to about 6.0 gms per two ounces of pasta. The preferred range of psyllium is from about 1.5 gms to about 4.0 gms per two ounces of pasta product.

It is preferred to use one of the standard flours used in the manufacture of pastas for the invention described herein. These include semolina flour, which is preferred, durum flour, farina flour, and all purpose flour, as well as any and all combinations of these. Also encompassed by the invention are those pasta products intended for those with wheat or gluten allergic, including pastas based on corn flour, jerusalem artichoke flour, and other non-wheat based products.

Flavor components, i.e., tomato, parsley, calamari, lemon, garlic, curry, carrot, porcini, mushroom, black pepper, beet, onion, basil, ginger, saffron, lime, sage, spinach, dill, cilantro, serrano, green pepper, tarragon and combinations thereof, can also be added to the pasta product of the present invention, as can colors, eggs or egg components, and other seasonings, preservatives, and so forth.

The pasta product may include products such as but not limited to, spaghetti, vermicelli, macaroni, linguini, Chinese or Japanese noodles, and buckwheat noodles.

These products may include so-called "fresh" pastas, as well as dried pastas, the latter being especially preferred. The dried pastas are expected to have a shelf life equivalent to pasta products which do not contain psyllium.

Further it is believed that other ingredients may be added to the pasta product without departing from the spirit and scope of the invention. Further, it is not intended that the present invention be limited to only the described embodiments. Modification of these embodiments will be recognized by those skilled in the art. Rather, the invention should be circumscribed by the scope of the appended claims.

We claim:

1. A pasta product comprising:
    a. at least one pasta flour; and
    b. prewetted psyllium.

2. The pasta product of claim 1, comprising about 1.0 g to about 6.0 g of psyllium per two ounces of pasta product.

3. The pasta product of claim 2, comprising from about 1.5 g to about 4.0 g of psyllium per two ounces of pasta product.

4. The pasta product of claim 1, wherein said prewetted psyllium is cold extruded.

5. The pasta product of claim 1, wherein said prewetted psyllium is hot extruded.

6. The pasta product of claim 1, further comprising an egg ingredient.

7. The pasta product of claim 1, wherein the pasta flour is selected from the group consisting of semolina flour, durum flour, farina flour, all-purpose flour, and combinations thereof.

8. The pasta product of claim 1, wherein the pasta flour is semolina flour.

9. The pasta product of claim 1, further comprising at least one flavor component.

10. The pasta product of claim 9, wherein the flavor component is selected from the group consisting of tomato, parsley, calamari, lemon, garlic, curry, carrot, porcini, mushroom, black pepper, beet, onion, basil, ginger, saffron, lime, sage, spinach, dill, cilantro, serrano, green pepper, tarragon and combinations thereof.

11. The pasta product of claim 1, which has a moisture content of at least 40%.

12. The pasta product of claim 1, which has a moisture content of at least about 45%.

13. Method of preparing a pasta product comprising:
    a. premixing psyllium with water to form a mixture;
    b. blending the resulting mixture of step (a) with a pasta flour so as to form a pasta dough; and
    c. extruding the pasta dough of step (b).

14. The method of claim 13, further comprising drying said extruded pasta dough.

15. Method of claim 13, wherein said pasta component is selected from the group consisting of semolina flour, durum flour, farina flour, all-purpose flour, and combinations thereof.

16. Method of claim 13, further comprising blending a flavor component with the pasta dough of step (b).

17. Method of claim 16, wherein said flavor component is selected from the group consisting of tomato, parsley, calamari, lemon, garlic, curry, carrot, porcini, mushroom, black pepper, beet, onion, basil, ginger, saffron, lime, sage, spinach, dill, cilantro, serrano, green pepper, tarragon and combinations thereof.

18. Method for reducing serum cholesterol in a subject comprising administering to said subject an amount of the pasta product of claim 1 sufficient to reduce the serum cholesterol level of said subject.

19. Pasta product produced by the process of claim 13.

20. Method for preparing a pasta product comprising:
a. forming an extruded psyllium pellet comprising psyllium, sweetening agent and flour;
b. grinding said extruded psyllium pellet to form a psyllium powder;
c. prewetting said psyllium powder to form a psyllium composition;
d. blending said psyllium composition obtained in step c. with a pasta flour so as to form a pasta dough; and
e. extruding the pasta dough of step d.

21. Method of claim 20, wherein the extruded psyllium pellet is formed by cold extrusion.

22. Method of claim 20, wherein the extruded psyllium pellet is formed by hot extrusion.

* * * * *